United States Patent [19]

Thoma

[11] Patent Number: 4,997,446
[45] Date of Patent: Mar. 5, 1991

[54] METHOD AND APPARATUS FOR OSSEOUS CONTOUR RECONSTRUCTION

[75] Inventor: Randall J. Thoma, Austin, Tex.

[73] Assignee: Intermedics Orthopedics, Inc., Austin, Tex.

[21] Appl. No.: 407,203

[22] Filed: Sep. 14, 1989

[51] Int. Cl.$^5$ .......................... A61F 2/28; A61B 17/56
[52] U.S. Cl. ........................................ 623/16; 606/77; 424/549
[58] Field of Search .................... 623/16, 66; 424/549; 606/76, 77, 60, 69, 72

[56] References Cited

U.S. PATENT DOCUMENTS

| | | | |
|---|---|---|---|
| 3,684,522 | 8/1972 | Stemmer et al. | 623/16 |
| 3,849,805 | 11/1974 | Leake et al. | 623/16 |
| 4,263,185 | 4/1981 | Belykh et al. | 606/76 X |
| 4,430,760 | 2/1984 | Smestad | 623/16 X |
| 4,637,931 | 1/1987 | Schmitz | 424/549 X |
| 4,674,488 | 6/1987 | Nashef et al. | 623/16 X |
| 4,755,184 | 7/1988 | Silverberg | 623/16 |
| 4,784,127 | 11/1988 | Mattheck et al. | 606/60 |

Primary Examiner—Alan W. Cannon
Attorney, Agent, or Firm—John R. Merkling

[57] ABSTRACT

A bone induction tray which acts as a structural support intimate contact with a bone to be repaired and participates directly in the reconstruction of a bone defect by providing direct chemical bonding with the bone and in the repair thereof. A suitable dimensionally formable fabric is selected which comprises a woven or non-woven mesh of fibers having pores between the fibers primarily for carrying an appropriate ceramic material therein. The fabric acts as a substrate support for a calcium phosphate biomaterial which is coated onto the fabric mesh such that the individual fibers of the mesh are completely coated and the pores in the mesh are completely impregnated therewith. Preferred bioresorbable fiber materials are the alpha-hydroxyacids such as lactic acid or glutaric acid. Preferred non-bioresorbable fabrics are typically polyamides, polyesters, or polyacrylics.

3 Claims, No Drawings

METHOD AND APPARATUS FOR OSSEOUS CONTOUR RECONSTRUCTION

BACKGROUND OF THE INVENTION

The present invention relates to bone induction tray devices for assisting in the reconstruction of bone defects and in particular to a device for participating directly in osseous contour reconstruction by structural support and chemical bonding. Prior try devices such as disclosed in U.S. Pat. No. 3,849,805 to Leake et al. are preconstructed prior to surgery in the approximate shape of the bone to be repaired and implanted after surgery is performed around the bone as a permanent structural support for containing autologous bone matter placed within a crevice or passage provided in the permanent structure.

SUMMARY OF THE INVENTION

The present invention provides a bone induction tray which acts as a structural support in intimate contact with a bone to be repaired and participates directly in the reconstruction of a bone defect by providing direct chemical bonding with the bone and in the repair thereof.

DETAILED DESCRIPTION OF PREFERRED EMBODIMENTS

Following is a description of preferred embodiments of the invention.

A suitable dimensionally formable fabric is selected which comprises a woven or non-woven mesh of fibers having pores between the fibers primarily for carrying an appropriate ceramic material therein. The fabric material is constructed by conventional means such as by weaving, needle punching or the like. The fibers typically comprises a synthetic material which may be either bioresorbable or non-bioresorbable, i.e. either soluble or insoluble in natural body fluids such as blood after extended exposure thereto.

The fabric acts as a substrate support for a calcium phosphate biomaterial which is coated onto the fabric mesh such that the individual fibers of the mesh are completely coated and the pores in the mesh are completely impregnated therewith. Preferred bioresorbable fiber materials are the alpha-hydroxyacids such as lactic acid or glutaric acid. Preferred non-bioresorbable fabrics are typically polyamides, polyesters, or polyacrylics.

The biomaterial typically comprises a ceramic material which has a chemical formula having two or more calcium ions and two or more phosphate ions. The ceramic material is further typically selected such that it is capable of forming a chemical bond with the bone to be repaired. A bioresorbable or non-bioresorbable ceramic may be used, the preferred bioresorbable ceramic being tricalcium phosphate, $Ca_3(PO_4)_2$, having either a beta-whitlockite or alpha-whitlockite crystal structure, and the preferred non-bioresorbable ceramic being hydroxylapatite $Ca_{10}(PO_4)_6(OH)_2$. Less preferred ceramic materials are calcium pyrophosphate $Ca_2P_2O_7$ and calcium phosphate oxide compounds, $XCaOP_2O_5$.

The ceramic material is typically pre-prepared by conventional means such as by prescription from aqueous solution to yield a porous material preferably having macropores greater than about 50 $\mu m$ and most preferably between about 100 and about 400 $\mu m$ for purposes of more readily enabling chemcial bonding with a bone substrate. The selected ceramic material is formed into a paste by addition of water to the dry ceramic and the paste is then applied to the selected fabric.

The coated fabric may be applied to the bone to be replaced and cured in alternative manners. In one embodiment of the invention, surgery is performed on the patient, the fabric is coated with the ceramic paste simultaneously with the performance of the surgery and the freshly coated fabric is wrapped around the bone area to be induced such that the ceramic material is affixed in intimate contact with the outside surface contour of the bone area to be induced. After the surgery is completed, the coated fabric cures in vivo into a hardened dimensionally stable structure in intimate contact with the bone. Over a period of time typically several weeks to several months, the ceramic material chemically bonds both to the outside surface of the bone and within discontinuities in the bone such that the bone is both supported by the dimensionally stable structure and assisted in the natural bone healing process by the tray device.

The coated fabric may alternatively be pre-coated, and pre-molded into the approximate shape of the bone to be repaired prior to actual surgery. In such an alternative embodiment the selected fabric is coated with the selected ceramic material in the form of a paste, the coated fabric is molded to the approximate shape of the outside contour of the bone to be induced, and the molded fabric is cured into a hardened dimensionally stable structure. Surgery is later performed and the pre-molded, pre-cured structure is implanted around the bone such that the ceramic material of the structure is affixed to the bone in intimate contact therewith.

In a most preferred embodiment of the invention the fabric component of the tray structure is selected to comprise a bioresorbable polymer and the ceramic is selected to comprise a non-bioresorbable biomaterial such that after a period of time, the fabric is resorbed away and the ceramic material is left behind chemically bonded to the bone.

The dimensionally stable, cured tray structures according to the invention may be used in conjunction with autologous bone chips which may be implanted in the area of the bone defect or discontinuity prior to the affixation of the tray structure to the surface of the bone. Where the tray structure is pre-molded and pre-curd prior to surgery, the tray structure may be provided with a crevice, slit, passage or the like for inserting analogous bone chips therein for eventual incorporation into a bone discontinuity.

The foregoing are specific examples of preparations of tray structures according to the invention.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A method for inducing bone formation comprising the steps of:
   selecting a dimensionally formable fabric comprising a web of fibers and an array of pores therebetween, the fibers comprising a polymer compound selected from the group of homopolymers, copolymers and terpolymers;

selecting a ceramic biomaterial having a chemical formula including more than one calcium cation and more than one phosphate anion, the ceramic material being chemically bondable to a bone without connective tissue intervening therebetween;

mixing the ceramic material with a predetermined amount of water to form a paste;

coating the ceramic material onto the fabric such that the fibers are completely coated and the pores are completely impregnated therewith;

forming the coated fabric into a shape complementary to the outside surface contour of a selected bone;

curing the shaped fabric into a dimensionally stable structure around the exposed bone such that the ceramic material is maintained in intimate contact with bone.

2. The method of claim 1 wherein the polymer compound is selected from the group of hydroxy acids, polyamides, polyesters, or polyurethanes.

3. The method of claim 1 wherein the biomaterial is selected from the group of alpha-whitlockite, beta-whitlockite, and hydroxyapatite.

* * * * *